United States Patent [19]

Milano

[11] Patent Number: 4,811,730
[45] Date of Patent: Mar. 14, 1989

[54] CPR FACE MASK AND METHOD OF USING SAME

[75] Inventor: Arthur J. J. Milano, Burlington, Conn.

[73] Assignee: Seitz Corporation, Torrington, Conn.

[21] Appl. No.: 220,539

[22] Filed: Jul. 18, 1988

[51] Int. Cl.$^4$ .............................................. A61M 16/00
[52] U.S. Cl. ........................ 128/203.11; 128/202.28; 128/202.29
[58] Field of Search ................. 128/202.28, 202.29, 128/203.11

[56] References Cited

U.S. PATENT DOCUMENTS

| | | | |
|---|---|---|---|
| 2,280,050 | 2/1942 | Alexander et al. | 128/203.11 |
| 2,850,011 | 9/1956 | Schaefer | 128/206.26 |
| 2,887,104 | 3/1958 | Sovinsky et al. | 128/203.11 |
| 3,017,880 | 11/1958 | Brook | 128/203.11 |
| 3,018,775 | 1/1962 | Wilson et al. | 128/203.11 |
| 3,099,985 | 8/1963 | Wilson et al. | 128/203.11 |
| 3,158,152 | 9/1960 | Bloom | 128/203.11 |
| 3,219,030 | 2/1962 | Bartlett | 128/203.11 |
| 3,242,921 | 3/1966 | Seeler | 128/203.11 |
| 3,286,710 | 2/1962 | Bartlett | 128/203.11 |
| 3,356,100 | 11/1962 | Seeler | 128/203.11 |
| 3,518,989 | 2/1966 | Seeler | 128/203.11 |
| 3,796,216 | 3/1974 | Schwarz | 128/203.11 |
| 3,923,054 | 12/1975 | Bauer, Jr. | 128/203.11 |
| 4,106,502 | 8/1978 | Wilson | 128/203.11 |
| 4,513,741 | 4/1985 | Demi | 128/206.26 |
| 4,579,114 | 4/1986 | Gray et al. | 128/203.11 |
| 4,601,465 | 7/1986 | Roy | 128/207.16 |

FOREIGN PATENT DOCUMENTS

| | | | |
|---|---|---|---|
| 185017 | 5/1907 | Fed. Rep. of Germany | 128/206.26 |

*Primary Examiner*—Edgar S. Burr
*Assistant Examiner*—Aaron J. Lewis

[57] ABSTRACT

A resuscitation mask has a base member with an inflatable bladder about its periphery which will rapidly and effectively seal against the face of the patient upon initial flow of air into the mask from the rescuer. A delivery member causes air to flow to the bladder to effect the inflation and then a valve member precludes further inflation. A one-way valve and filter in the conduit from the delivery member to the base member precludes flow of air and body fluids from the patient to the mouthpiece, and diverts exhaled air to the atmosphere about the mask.

13 Claims, 5 Drawing Sheets

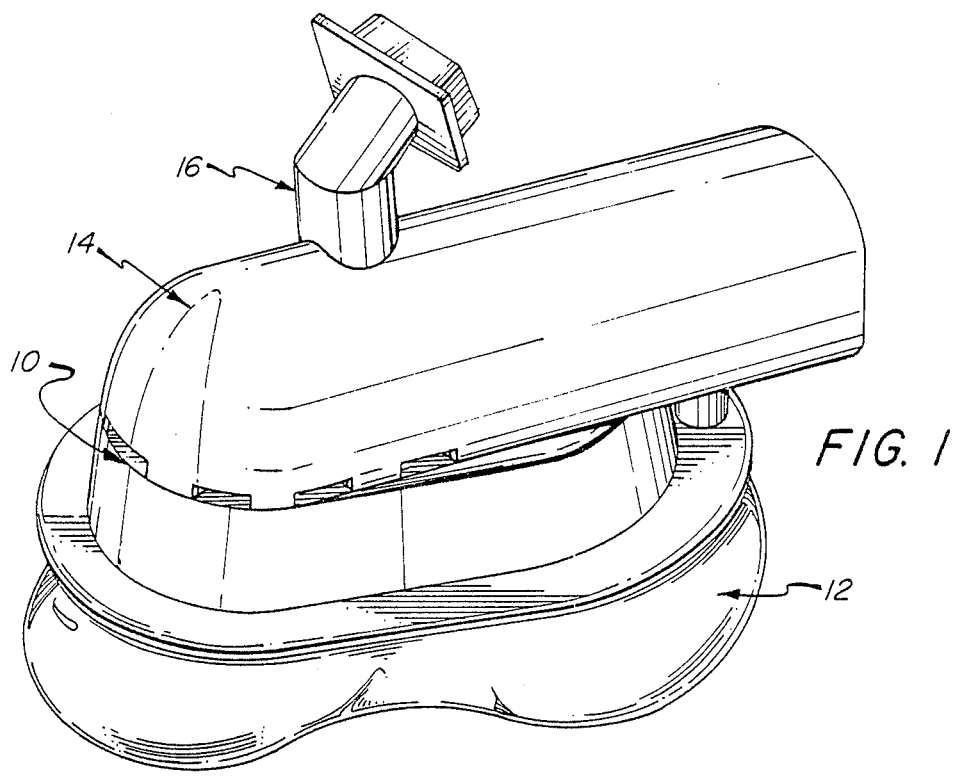
FIG. 1
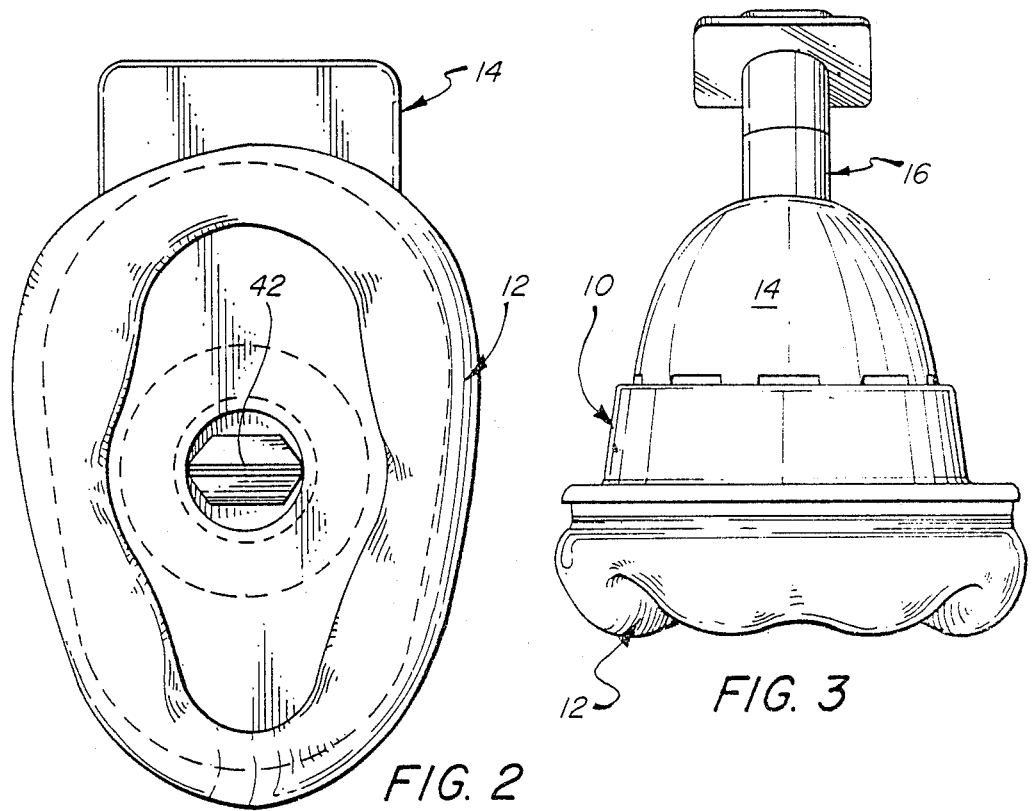
FIG. 2
FIG. 3

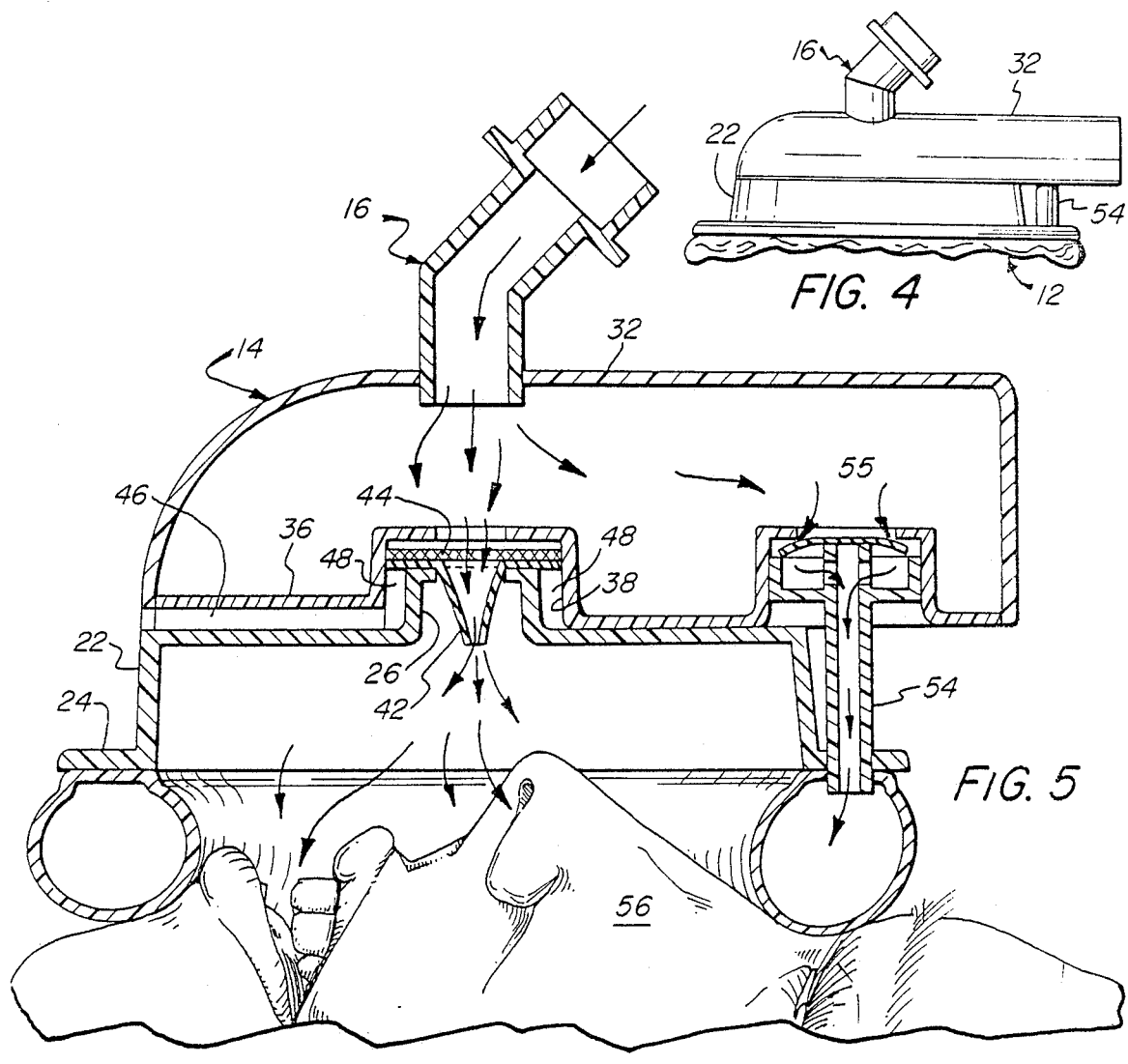
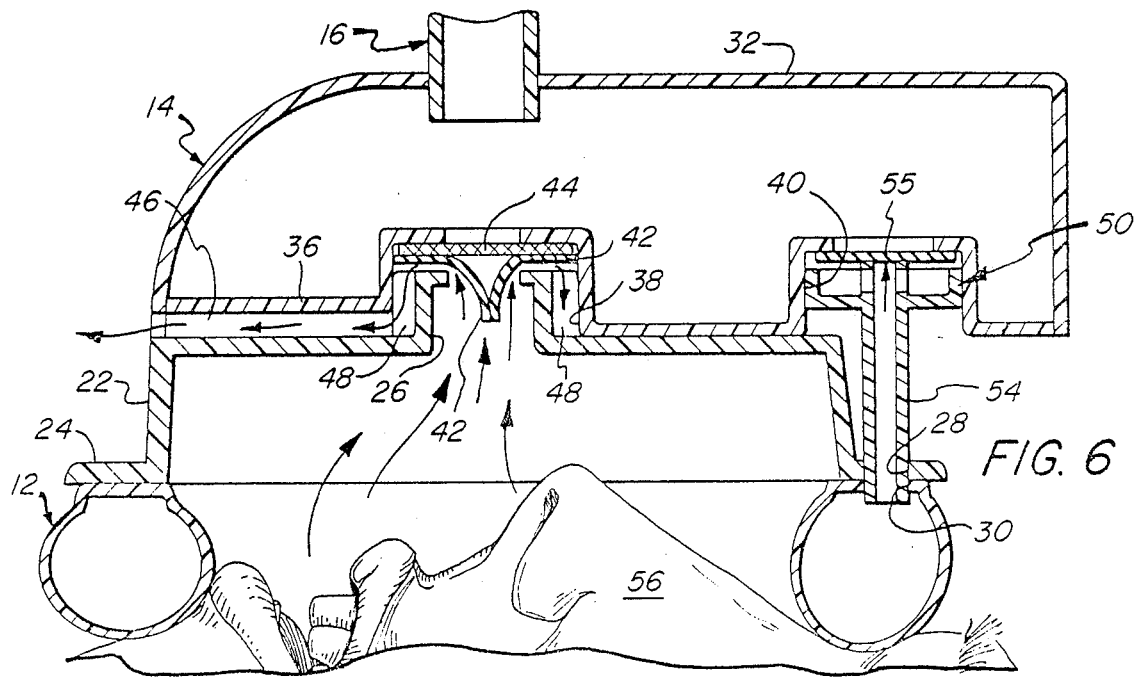

CPR FACE MASK AND METHOD OF USING SAME

BACKGROUND OF INVENTION

Mouth-to-mouth resuscitation is widely employed in a number of life-saving situations, and various of devices have been developed to facilitate transfer of air from the mouth of the rescuer into the mouth and/or mouth and nose of the patient. Some of these devices comprise masks which fit over nose and mouth of the patient, and some include valves and fitters to preclude vomit or other fluids from reaching the rescuer.

In such masks, it is desirable that there be effective sealing about the periphery of the mask against the face of the user so that the plenum chamber formed within the mask can be effective in forcing air into the patient's lungs. Variations in the size ad contour of the facial area to be encompassed due to the size of the patient often require multiple size masks or some form of flexible seal to accommodate the variations in facial contour and facial size.

It is an object of the present invention to provide a novel mouth-to-mouth resuscitation mask which is readily adapted to seal effectively and rapidly against the face of user having a wide variety of facial sizes and contours.

It is also an object to provide such a mask in which reverse flow of air and fluids from the patient to the rescuer is effectively precluded.

Another object is to provide such a mask which may be assembled easily from relatively inexpensive components.

SUMMARY OF THE INVENTION

It has now been found that the foregoing and related objects and advantages may be readily attained in a mouth-to-mouth resuscitation device which has a base member with a top wall and a depending sidewall extending about its periphery to define a plenum chamber within the base member, and an inflatable bladder extending about the periphery of the base member and adapted to form a seal about the nose and mouth of a patient.

A delivery member is disposed above the base member and has a first conduit communicating with the plenum chamber, a second conduit communicating with the bladder, and an air feed orifice for introduction of air thereinto. A one-way valve means is located in the first conduit to permit passage of air from the delivery member into the plenum chamber and to preclude movement of air in the reverse direction. A pressure responsive valve means is disposed in the second conduit to permit passage of air into the bladder to effect inflation thereof, and this valve means seals to further flow of air therethrough upon establishment of a predetermined pressure in the bladder.

In the preferred embodiments, the base member has a flange extending outwardly about the lower end of the peripheral side wall. This flange may have a downwardly opening channel extending thereabout in which the upper end of the bladder is seated, and one of the bladder and channel may have a multiplicity of projections extending into recesses in the other.

Desirably, a filter means is provided in the first conduit to block contaminants from passing therethrough. Conveniently, the delivery member includes a depending detachable filter retaining member providing a portion of the first conduit and providing a chamber in which the one-way valve means is disposed with the filter means being disposed above the valve means. This filter member construction has passages venting to atmosphere below the valve means, and it may have a depending tubular portion registering with a passage in the top wall of the base member which snugly seats in an aperture in the top wall.

The delivery member has a passage therein between the orifice and conduits, and this passage extends laterally. The delivery member is dimensioned and configured to extend between the central portion of the base member and the periphery of the base member to which the bladder is secured. The second conduit communicates with a flexible conduit element on the base member communicating with the bladder member. Desirably, there is included a mouthpiece secured to the orifice.

BRIEF DESCRIPTION OF THE DRAWINGS

FIG. 1 is a perspective view of a resuscitation mask embodying the present invention;

FIG. 2 is a bottom view thereof;

FIG. 3 is an end elevational view thereof;

FIG. 4 is a side elevational view thereof drawn to a reduced scale;

FIG. 5 is a sectional view drawn to an enlarged scale thereof with the mask applied to the fragmentary illustrated head of a patient and including arrows to show the path of air blown through the mouthpiece by a rescuer (not shown) and with the bladder inflated;

FIG. 6 is a view similar to FIG. 5 schematically showing the path of air exhaled by the patient;

DETAILED DESCRIPTION OF PREFERRED EMBODIMENT OF THE INVENTION

Figure 7:
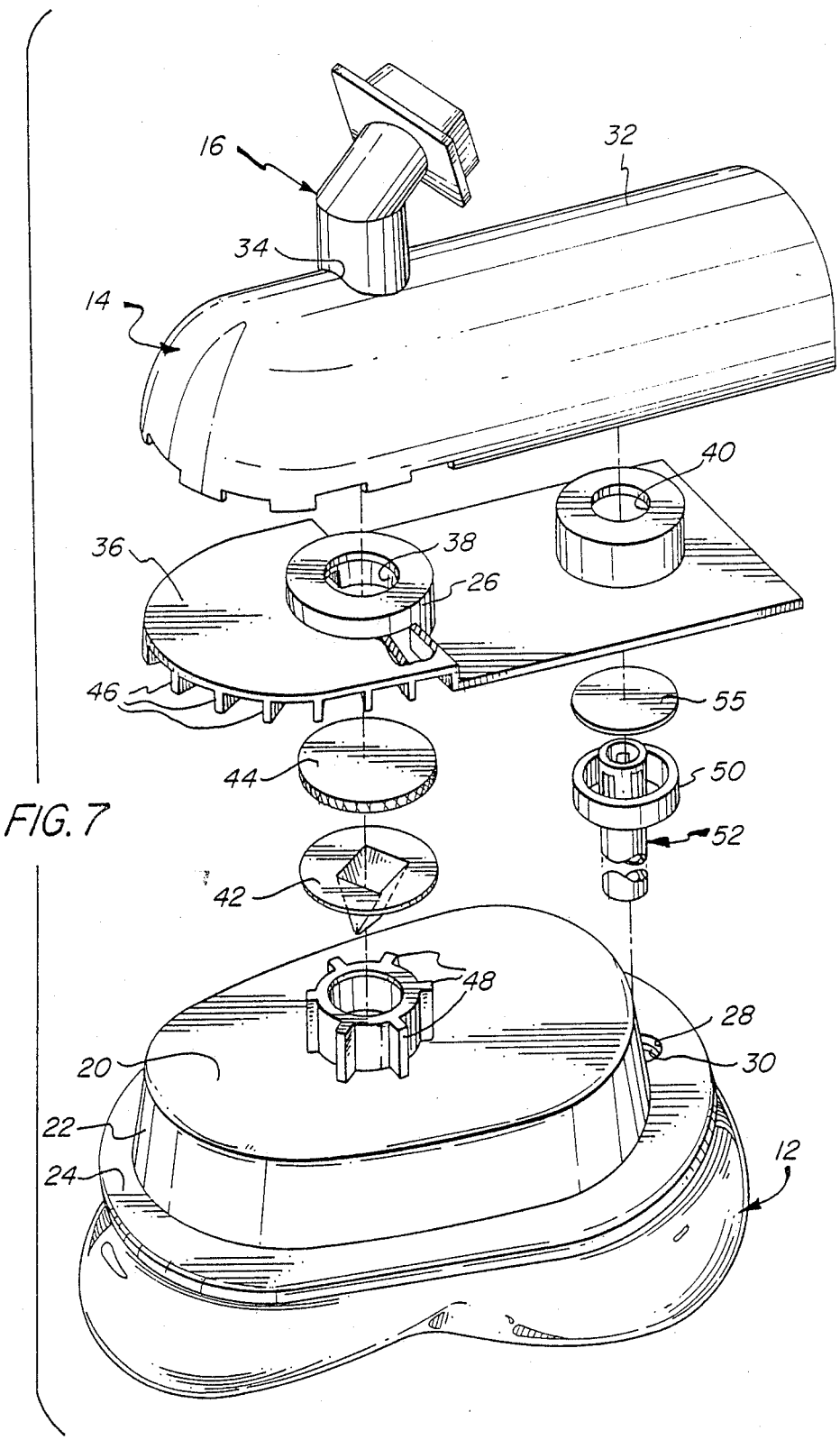
FIG. 7 is an partially exploded isometric view of the resuscitation mask of FIGS. 1–6.

Turning first to the embodiment of FIGS. 1–7, the mask is comprised of a base member generally designated by the numeral 10, a bladder extending thereabout and generally designated by the numeral 12, a delivery member generally designated by the numeral 14, and a mouthpiece generally designated by the numeral 16.

The base member 10 has a top wall 20, a depending peripheral sidewall 22, and a flange 24 extending outwardly about the lower periphery of the sidewall 22. As best seen in FIG. 1, the base member 10 is elongated and generally tear-drop in configuration. The top wall 20 and sidewall 22 define a plenum chamber therewithin adapted to encompass and receive the nose and mouth of a patient. The top wall 20 has an upwardly extending tubular extension 26 thereon, and the flange 24 has an aperture 28 therein.

The bladder 12 is of generally circular or tubular cross section and is adhesively bonded to the lower surface of the flange 24. It has an aperture 30 therein aligned with the aperture 28 in the flange 24.

The delivery member 14 is comprised of an outer shell 32 of generally inverted dish-shaped configuration with an aperture 34 therein, and an inner transverse wall element 36 providing a pair of tubular pockets 38 and 40. The tubular extension 26 on the top wall 20 of the base member 10 seats in the pocket 38 and terminates below the inner end thereof. Seated in the spacing between the end of the extension 26 and the flange at the inner end of the pocket 38 are a one-way valve member 42 and a gauze filter 44.

As best seen in FIG. 6, the tubular extension 26 has a series of axially extending ribs 44 on its outer surface which snugly seat it within the pocket 38 and provide air passages between the opposed walls. Ribs 46 on the outer surface of the wall element 36 radiating from the periphery of the pocket 38 provide air passages extending to the outer margins of the mask.

Snugly seated in the outer portion of the pocket 40 is the cup-shaped portion 50 of the conduit member generally designated by the numeral 52, and the tubular portion 54 extends therefrom through the aperture 28 in the base member flange 24 and the aperture 30 into the bladder 12. Disposed in the space above the tubular portion 54 is the flutter valve member 55.

Seated in the aperture 34 of the outer shell 32 is the generally tubular mouthpiece 16 to complete the assembly.

Although the wall element 36 can be frictionally secured in the outer shell 32, it is desirably adhesively bonded by ultrasonic welding, application of a separate adhesive coating or solvent bonding. Frictional engagement may be relied upon to secure the tubular extension and conduit members in the pockets, but this may be augmented by adhesive action is so desired.

To assemble the elements, the wall element 36 is assembled with the outer shell 32 to form the delivery member 14. The gauze filter 44 and duck-bill valve member 42 are placed in the pocket 38, and the flutter valve member 55 and cup-shaped portion 50 of the conduit member are placed in the pocket 40. The base member 10 is then assembled with the bladder 12, and this subassembly is aligned with the previously assembled components. The tubular extension 26 is frictionally engaged in the pocket 38, and the conduit member is frictionally engaged in the apertures 28 and 30.

In operation, the base member 10 is placed over the face of the patient 56, and the rescuer blows into the mouthpiece 16, initially causing the periphery of the flutter valve member 55 to deflect and allow air to flow into the bladder 12 to inflate it into sealing engagement with the face 56 of the patient until the pressure within the bladder 12 causes the valve member 55 to seat against the upper end of the pocket 40 to seal the passage. Air continues to flow into the pocket 38 through the filter 44 and the duck-bill valve member 42 which is pressed downwardly against the tubular extension 26. Air then flows into the plenum chamber of the mask.

When the patient exhales, the air lifts the duck-bill valve member 42 (and gauze filter 44) upwardly from the tubular extension 26, and it flows downwardly in the spacing between the ribs 46 about the tubular extension 26 and outwardly to the atmosphere in the channels between the ribs 48.

Figure 8:
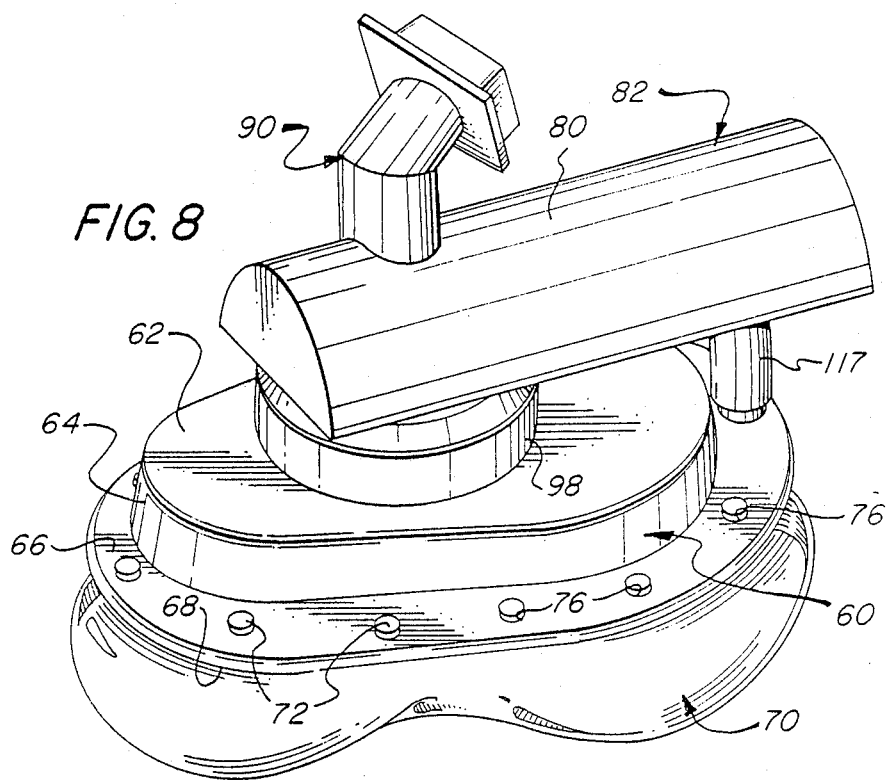
FIG. 8 is a perspective view of another mask embodying the present invention.
Figure 9:
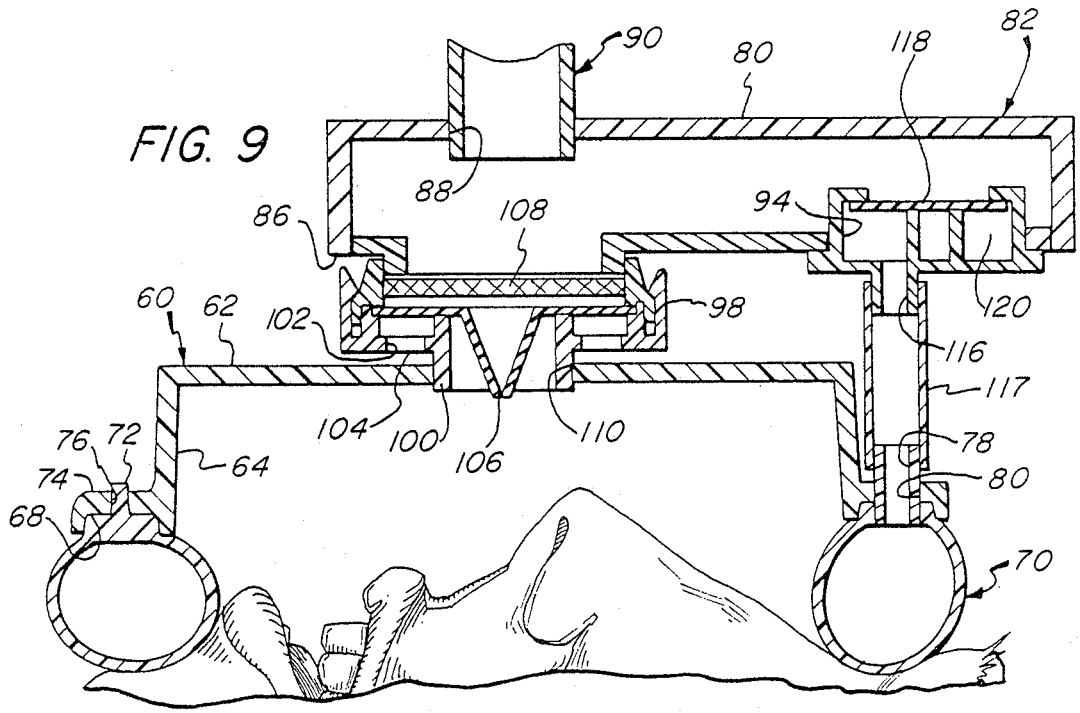
FIG. 9 is a sectional view thereof.
Figure 10:
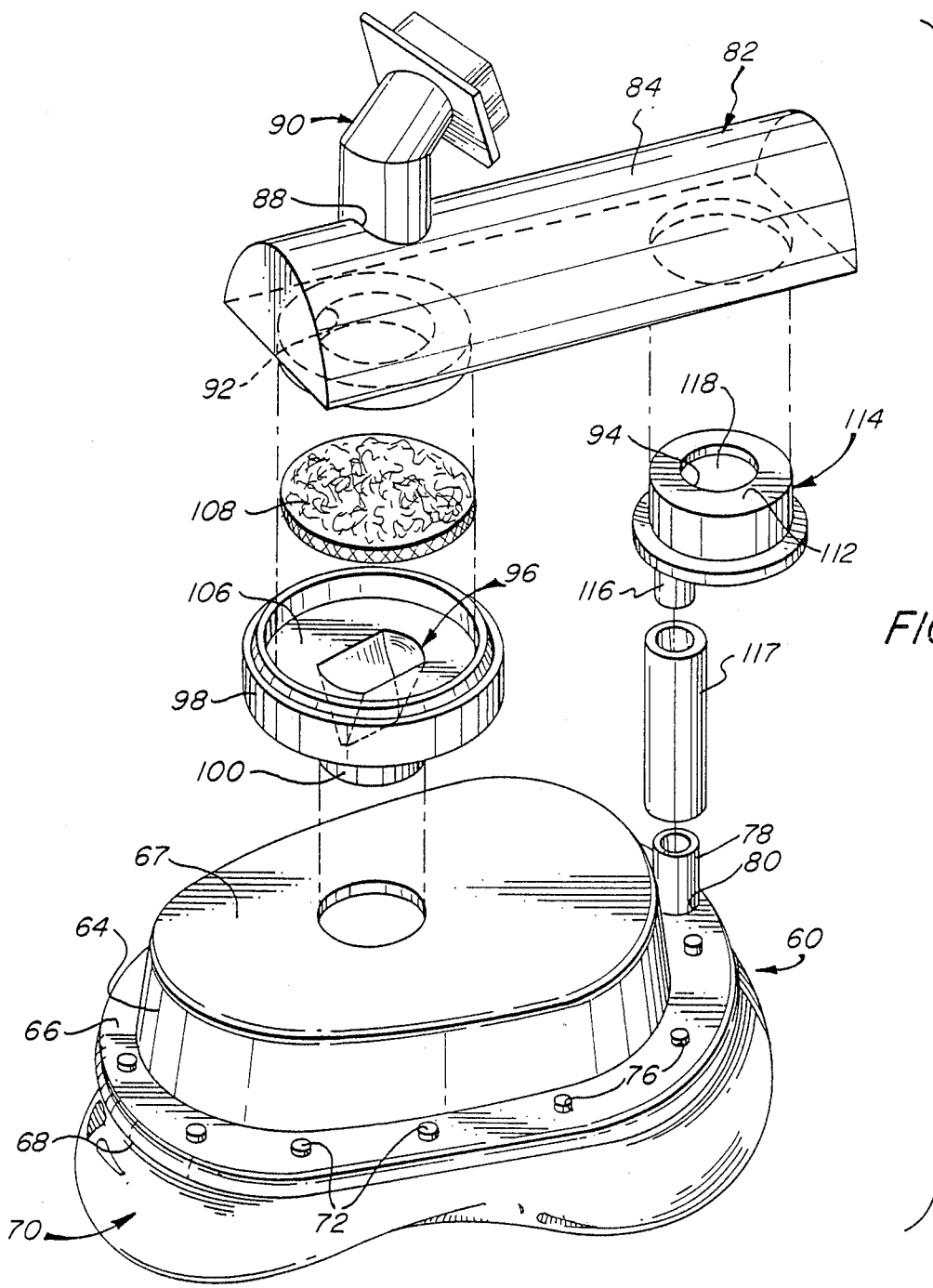
FIG. 10 is a partially exploded isometric view thereof.

Turning now to the embodiment of FIGS. 8-10, the base member generally designated by the numeral 60 has a top wall 62, peripheral sidewall 64, and flange 66 with a downwardly opening channel 68. The bladder generally designated by the numeral 70 has upstanding bosses 72 on a shoulder 74 which seats within the channel 68, and these bosses 72 seat in apertures 76 in the flange 66. A tubular conduit 78 extends upwardly therefrom through an aperture 80 in the flange 66.

The delivery member generally designated by the numeral 82 is comprised of the outer shell 84 and cover element 86. The shell 84 has an orifice 88 in which the mouthpiece 90 is seated. The cover element 86 is formed with pockets 92 and 94 which have perforate upper walls.

Seated in the pocket 92 is the delivery valve member generally designated by the numeral 96, and it has a cup-shaped portion 98 with a depending tubular portion 100. The cup-shaped portion 98 has apertures 102 in its transverse wall 104 about the tubular portion 100. Seated on the transverse wall 104 is the duck-bill one way valve member 106, and a gauze filter 108 is disposed thereon. The tublar portion 100 frictionally seats in the aperture 110 in the top wall 62 of the base member 60.

Seated in the pocket 94 is the cup shaped portion 112 of the bladder valve member 114, and a tubular conduit portion 116 couples with the conduit 78 of the bladder 70 through the flexible coupling 117. Seated in the recess provided by the cup-shaped portion 112 is a flutter valve 118 which, under air pressure from below, will seat against the surface of the pocket 94 about the air passage 120.

In operation, air entering through the mouthpiece 90 flows through the delivery valve member 96 to the pocket 94 where it deflects the flutter valve member 118 and flows to the bladder 70 to inflate it until the air pressure forces the valve member 118 to seat against the surface of the pocket 94 about the air passage 120. Air flows through the gauze filter 108 and duck-bill valve member 106 into the chamber formed by the base member 60. Upon exhalation by the patient, the air enters the delivery valve member tubular portion 100 and is deflected by the valve member 106 through the discharge apertures 102 in the transverse wall 104.

In both embodiments, the base member, delivery member, and mouthpiece (and delivery valve member and bladder valve member of the embodiment of FIGS. 8-10) may be readily fabricated by injection molding or other suitable processes from synthetic resins such as polyvinyl chloride, high impact polystyrene, and ABS which provide a reasonable degree of transparency in addition to durability. The bladder is conveniently formed from a flexible resin such as polyurethane.

Thus, it can be seen that the resuscitation mask described and illustrated in the foregoing detailed description and attached drawings provides a novel and effective means for expedited mouth-to-mouth resuscitation with good sealing action to the face of the patient. Exhaled air and fluids from the patient are precluded from reaching the rescuer. Moreover, the components may be readily and economically fabricated and assembled.

I claim:

1. In a mouth-to-mouth resuscitation device, the combination comprising:

(a) a base member having a top wall and a depending sidewall extending about its periphery to define a plenum chamber within said base member;

(b) an inflatable bladder extending about the periphery of said base member and adapted to form a seal about the nose and mouth of a patient;

(c) a delivery member above said base member having a first conduit communicating with, said plenum chamber, a second conduit communicating with said bladder, and said plenum chamber, and an air feed orifice for introduction of air thereinto;

(d) one-way valve means in said first conduit to permit passage of air from said delivery member into said plenum chamber and to preclude movement of air in the reverse direction; and (e) pressure responsive valve means in said second conduit permitting passage of air into said bladder to effect inflation thereof, said valve means automatically sealing in response to pressure within said bladder to prevent further flow of air therethrough upon establishment of a predetermined pressure in said bladder.

2. The resuscitator of claim 1 wherein said base member has a flange extending outwardly about the lower end of said peripheral side wall.

3. The resuscitator of claim 2 wherein said flange has a downwardly opening channel extending thereabout in which the upper end of said bladder is seated.

4. The resuscitator of claim 3 wherein one of said bladder and said channel has a multiplicity of projections extending into recesses in the other.

5. The resuscitator of claim 1 wherein there is included a filter means in said first conduit to block contaminants from passing therethrough.

6. The resuscitator of claim 5 wherein said delivery member includes a depending detachable filter retaining member providing a portion of said first conduit and providing a chamber in which said one-way valve means is disposed, said filter means being disposed above said valve means.

7. The resuscitator of claim 6 wherein said filter member has passages venting to atmosphere below said valve means.

8. The resuscitator of claim 6 wherein said filter member has a depending tubular portion registering with a passage in said top wall of said base member.

9. The resuscitator of claim 8 wherein said depending tubular portion snugly seats in an aperture in said top wall.

10. The resuscitator of claim 1 wherein said delivery member has a passage therein between said orifice and said conduits.

11. The resuscitator of claim 10 wherein said passage extends laterally and said delivery member is dimensioned an configured to extend between the central portion of said base member and the periphery of the base member to which said bladder is secured.

12. The resuscitator of claim 11 wherein said second conduit communicates with a flexible conduit element on said base member communicating with said bladder.

13. The resuscitator of claim 1 wherein there is included a mouthpiece secured to said orifice.

* * * * *